United States Patent [19]

Massonne et al.

[11] Patent Number: 5,393,874
[45] Date of Patent: Feb. 28, 1995

[54] PREPARATION OF N-HYDROXY-N'-DIAZENIUM OXIDES

[75] Inventors: Klemens Massonne, Westheim; Martin Fischer, Ludwigshafen, both of Germany

[73] Assignee: BASF Aktiengesellschaft, Ludwigshafen, Germany

[21] Appl. No.: 120,338

[22] Filed: Sep. 14, 1993

[30] Foreign Application Priority Data

Sep. 18, 1992 [DE] Germany .............................. 4231296

[51] Int. Cl.⁶ .................... C07C 245/04; C07C 245/02
[52] U.S. Cl. ..................................... 534/556; 534/568; 534/572; 534/565
[58] Field of Search ......................... 534/556, 572, 568

[56] References Cited

FOREIGN PATENT DOCUMENTS 1019657 5/1958 Germany .............. 534/557
1543375 1/1970 Germany .............. 534/557
815537 6/1959 United Kingdom ................ 534/557

OTHER PUBLICATIONS

Japanese Abstract 49/80023 Fujitsuka et al. (1974).

Primary Examiner—Floyd D. Higel
Attorney, Agent, or Firm—Keil & Weinkauf

[57] ABSTRACT

The preparation of N-hydroxy-N'-diazenium oxides of the general formula I

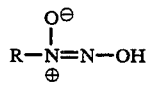

where R is an aliphatic or cycloaliphatic radical, by reacting a hydroxylamine of the general formula II

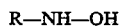

or its salt with nitrosyl chloride or nitrosylsulfuric acid in aqueous solution is described.

The process products are intermediates for fine chemicals and are used in the form of their metal salts as wood preservatives.

6 Claims, No Drawings

PREPARATION OF N-HYDROXY-N'-DIAZENIUM OXIDES

The present invention relates to a novel process for preparing N-hydroxy-N'-diazenium oxides of the general formula I

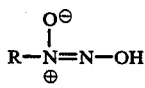

where R is an aliphatic or cycloaliphatic radical.

Aliphatic N-hydroxy-N'-diazenium oxides can be prepared according to DE-A 1 543 375 by photoreaction of the corresponding aliphatics with NO.

Furthermore, according to DE-A 1 019 657, the reaction of aliphatic hydroxylamines with alkali metal nitrites leads to the desired products. In this case, stoichiometric amounts of alkali metal salts are obtained as by-products.

JP-A 49/80023 describes the reaction of substituted hydroxylamines with salts or organic esters of nitrous acid in organic solvents. In this case too, stoichiometric amounts of alkali metal salts or organic by-products result.

It is an object of the present invention to make available a process for preparing aliphatic or cycloaliphatic N-hydroxy-N'-diazenium oxides which does not have the disadvantages mentioned.

We have found that this object is achieved by the process defined above, which comprises reacting a hydroxylamine of the general formula II

or its salt with nitrosyl chloride or nitrosylsulfuric acid in aqueous solution.

The process according to the invention can be represented schematically as follows:

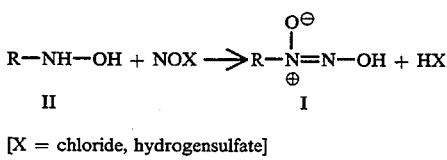

[X = chloride, hydrogensulfate]

The starting compounds II are known or accessible by known methods, for example by reduction of corresponding oximes. The radical R is an aliphatic or cycloaliphatic radical. This radical can carry substituents which are inert under the reaction conditions, such as halogen atoms. However, alkyl and cycloalkyl are preferred, in particular $C_3$–$C_{10}$-alkyl such as n-propyl, isopropyl, isobutyl or hexyl or $C_5$–$C_{10}$-cycloalkyl, cyclohexyl being preferred. The compounds II are preferably employed in the form of their salts, e.g. as hydrochloride or hemisulfate. Nitrosyl chloride, but preferably nitrosylsulfuric acid, is employed as the nitroso compound. The nitrosylsulfuric acid is as a rule present as a 5–60% strength by weight, preferably 20–50% strength by weight, solution in sulfuric acid.

The reaction of II with nitrosyl chloride or nitrosylsulfuric acid is performed in aqueous solution, preferably in dilute sulfuric acid. The product can be employed directly in the reaction solution for subsequent reactions. As the reaction product is only stable in the reaction solution for a short time, however, in a preferred embodiment it is removed therefrom by extracting with an organic solvent. Extracting agents which may be mentioned are particularly aliphatic hydrocarbons such as pentane, hexane and heptane, cycloaliphatic hydrocarbons such as cyclohexane, aromatic hydrocarbons such as benzene, toluene and xylene, halogenated hydrocarbons such as dichloromethane, chloroform and chlorobenzene and also aliphatic ethers such as diethyl ether and methyl tert-butyl ether, which can of course also be used mixed with one another. The amount of the extracting agent is expediently selected such that a 0.1–30% strength by weight, preferably 3–10% strength by weight, solution of I is obtained.

In a particularly preferred embodiment, the reaction is performed in the presence of an extracting agent.

Acid formed in the reaction can be recycled.

The temperature is as a rule from the solidification point of the aqueous reaction mixture (about −20° C.) to 60° C.

At these temperatures, the reaction is in general complete in less than an hour.

The process can be carried out either continuously or batchwise.

As the compounds I are stable only for a limited time even in the extraction solution, as a rule their preparation is followed by a reaction for converting them into more stable salts according to known methods. Ammonia, primary amines, transition metal salts such as copper sulfate or nickel nitrate, for example, but preferably potassium hydroxide, are suitable for forming salts.

The process according to the invention converts hydroxylamines into N-hydroxy-N'-diazenium oxides without salts or organic compounds being obtained as by-products, and it enables the preparation of concentrated solutions of the product.

The process products are employed as wood-impregnating agents, e.g. in the form of their copper salts (DE-A 2 410 603).

EXAMPLE 18.7 g (61 mmol) of 41.7% strength by weight nitrosylsulfuric acid in sulfuric acid were added at 8° C. to 10.1 g (61 mmol) of cyclohexylhydroxylamine hemisulfate, 306 g of 20% strength by weight sulfuric acid and 270 g of toluene. After 20 minutes, the organic phase was separated off and treated with 20 ml of water. The pH of the aqueous phase was adjusted to 11.5 using 50% strength potassium hydroxide solution. After extraction, 33.4 g of an aqueous phase were isolated which contained 26.7% by weight of the potassium salt of N'-cyclohexyl-N-hydroxy-diazenium-N'-oxide (49 mmol; 81% yield).

We claim:

1. A process for preparing N-hydroxy-N'-diazenium oxides of the formula I

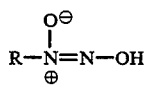

where R is an $C_3$–$C_{10}$-alkyl or $C_5$–$C_{10}$-cycloalkyl radical, which comprises reacting a hydroxylamine of formula II

or its salt with nitrosylsulfuric acid in aqueous solution.

2. A process as claimed in claim 1, wherein R is cyclohexyl.

3. A process as claimed in claim 1, wherein N-hydroxy-N'-diazenium oxide I is extracted from the reaction solution using an organic solvent.

4. A process as claimed in claim 2, wherein the N-hydroxy-N'-diazenium oxide I is extracted from the reaction solution using an organic solvent.

5. A process as claimed in claim 1, wherein the reaction is performed in the presence of an organic extracting agent.

6. A process as claimed in claim 2, wherein the reaction is performed in the presence of an organic extracting agent.

* * * * *